(12) United States Patent
Roe et al.

(10) Patent No.: US 9,089,456 B2
(45) Date of Patent: Jul. 28, 2015

(54) REUSABLE OUTER COVER FOR AN ABSORBENT ARTICLE HAVING ZONES OF VARYING PROPERTIES

(71) Applicant: The Procter & Gamble Company, Cincinnati, OH (US)

(72) Inventors: Donald Carroll Roe, West Chester, OH (US); Elaine Mary Wiggins, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 134 days.

(21) Appl. No.: 13/858,962

(22) Filed: Apr. 9, 2013

(65) Prior Publication Data

US 2013/0226122 A1    Aug. 29, 2013

Related U.S. Application Data

(62) Division of application No. 12/687,528, filed on Jan. 14, 2010, now Pat. No. 8,435,223.

(60) Provisional application No. 61/144,883, filed on Jan. 15, 2009.

(51) Int. Cl.
| | |
|---|---|
| *A61F 13/15* | (2006.01) |
| *A61B 9/00* | (2006.01) |
| *A61F 13/505* | (2006.01) |
| *A61F 13/49* | (2006.01) |
| *A61F 13/56* | (2006.01) |

(52) U.S. Cl.
CPC ......... *A61F 13/505* (2013.01); *A61F 13/49003* (2013.01); *A61F 13/49014* (2013.01); *A61F 13/5622* (2013.01)

(58) Field of Classification Search
CPC ................ A61F 13/49003; A61F 2013/51423; A61F 2013/51443; A61F 2013/51447; A61F 2013/51449; A61F 2013/51452; A61F 2013/15276; A61F 2013/15552
See application file for complete search history.

(56) References Cited

U.S. PATENT DOCUMENTS

| | | | |
|---|---|---|---|
| 2,503,647 | A | 11/1950 | Buchler |
| 2,688,328 | A | 9/1954 | Marcus |
| 2,793,642 | A | 5/1957 | Andruhovici |
| 3,077,193 | A | 2/1963 | Mann |

(Continued)

FOREIGN PATENT DOCUMENTS

| | | |
|---|---|---|
| AU | 642 386 | 10/1993 |
| CA | 2 103 537 | 2/1995 |

(Continued)

OTHER PUBLICATIONS www.gdiapers.com—Web pages dated Nov. 23, 2009.

(Continued)

*Primary Examiner* — Susan Su
(74) *Attorney, Agent, or Firm* — Sarah M. DeCristofaro; Abbey A. Lopez (57) ABSTRACT

An absorbent article having a reusable outer cover and, optionally, an absorbent insert. The reusable outer cover has zones of varying properties. The properties of the different zones are varied to provide different performance features in different parts of the outer cover. The outer cover with zones of varying properties may provide competing or contradictory functionalities for improved comfort, fit, leakage protection, and aesthetic appeal.

6 Claims, 2 Drawing Sheets

(56) References Cited

U.S. PATENT DOCUMENTS

| | | |
|---|---|---|
| 3,496,259 A | 2/1970 | Guenther |
| 3,560,292 A | 2/1971 | Butter |
| 3,574,791 A | 4/1971 | Patsy et al, |
| 3,719,736 A | 3/1973 | Woodruff |
| 3,735,424 A | 5/1973 | Maggio et al. |
| 3,860,003 A | 1/1975 | Buell |
| 3,911,173 A | 10/1975 | Sprague, Jr. |
| 3,926,189 A | 12/1975 | Taylor |
| 3,929,135 A | 12/1975 | Thompson |
| 3,955,575 A | 5/1976 | Okuda |
| 4,022,210 A | 5/1977 | Glassman |
| 4,072,150 A | 2/1978 | Glassman |
| 4,081,301 A | 3/1978 | Buell |
| 4,116,892 A | 9/1978 | Schwarz |
| 4,223,059 A | 9/1980 | Schwarz |
| 4,265,245 A | 5/1981 | Glassman |
| 4,284,454 A | 8/1981 | Joa |
| 4,324,246 A | 4/1982 | Mullane et al. |
| 4,326,302 A | 4/1982 | Lowe et al. |
| 4,338,939 A | 7/1982 | Daville |
| 4,342,314 A | 8/1982 | Radel et al. |
| 4,352,356 A | 10/1982 | Tong |
| 4,397,646 A | 8/1983 | Daniels et al. |
| 4,438,167 A | 3/1984 | Schwarz |
| 4,463,045 A | 7/1984 | Ahr et al. |
| 4,475,912 A | 10/1984 | Coates |
| 4,573,986 A | 3/1986 | Minetola et al. |
| 4,578,069 A * | 3/1986 | Whitehead et al. ............ 604/370 |
| 4,578,073 A | 3/1986 | Dysart et al. |
| 4,579,556 A | 4/1986 | Mcfarland |
| 4,582,550 A | 4/1986 | Sigl |
| 4,597,760 A | 7/1986 | Buell |
| 4,597,761 A | 7/1986 | Buell |
| 4,609,518 A | 9/1986 | Curro et al. |
| 4,610,678 A | 9/1986 | Weisman et al. |
| 4,610,681 A * | 9/1986 | Strohbeen et al. ............ 604/396 |
| 4,615,695 A | 10/1986 | Cooper |
| 4,629,643 A | 12/1986 | Curro et al. |
| 4,643,726 A | 2/1987 | Gegelys |
| 4,650,483 A | 3/1987 | Joffe |
| 4,657,539 A | 4/1987 | Hasse |
| 4,661,102 A | 4/1987 | Shikata et al. |
| 4,673,402 A | 6/1987 | Weisman et al. |
| 4,695,278 A | 9/1987 | Lawson |
| 4,701,170 A | 10/1987 | Wilson et al. |
| 4,704,114 A | 11/1987 | Wilson et al. |
| 4,710,187 A | 12/1987 | Boland et al. |
| 4,747,846 A | 5/1988 | Boland et al. |
| 4,756,709 A | 7/1988 | Stevens |
| 4,770,656 A | 9/1988 | Proxmire et al. |
| 4,785,996 A | 11/1988 | Ziecker et al. |
| 4,795,452 A | 1/1989 | Blaney et al. |
| 4,795,454 A | 1/1989 | Dragoo |
| 4,808,176 A | 2/1989 | Kielpikowski |
| 4,808,177 A | 2/1989 | Desmarais et al. |
| 4,808,178 A | 2/1989 | Aziz et al. |
| 4,816,026 A | 3/1989 | Richardson |
| 4,834,735 A | 5/1989 | Alemany et al. |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,872,871 A | 10/1989 | Proxmire et al. |
| 4,888,231 A | 12/1989 | Angstadt |
| 4,892,536 A | 1/1990 | Desmarais et al. |
| 4,892,598 A | 1/1990 | Stevens et al. |
| 4,906,243 A | 3/1990 | Dravland |
| 4,908,247 A | 3/1990 | Baird et al. |
| 4,909,803 A | 3/1990 | Aziz et al. |
| 4,936,840 A | 6/1990 | Proxmire |
| 4,955,880 A | 9/1990 | Rodriquez |
| 4,961,736 A | 10/1990 | McCloud |
| 4,964,857 A | 10/1990 | Osborn |
| 4,968,311 A | 11/1990 | Chickering et al. |
| 4,968,312 A | 11/1990 | Khan |
| 4,978,046 A | 12/1990 | Hagmann et al. |
| 4,981,480 A | 1/1991 | Gaudet et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,019,068 A | 5/1991 | Perez et al. |
| 5,021,051 A | 6/1991 | Hiuke |
| 5,032,120 A | 7/1991 | Freeland et al. |
| 5,037,416 A | 8/1991 | Allen et al. |
| 5,069,672 A | 12/1991 | Wippler et al. |
| 5,087,253 A | 2/1992 | Cooper |
| 5,098,419 A * | 3/1992 | Gold ............................ 604/396 |
| 5,108,385 A | 4/1992 | Snyder |
| 5,127,108 A | 7/1992 | Weiss |
| 5,137,537 A | 8/1992 | Herron et al. |
| 5,141,870 A | 8/1992 | Bedbrook et al. |
| 5,147,345 A | 9/1992 | Young et al. |
| 5,156,793 A | 10/1992 | Buell et al. |
| 5,167,897 A | 12/1992 | Weber et al. |
| 5,185,011 A | 2/1993 | Strasser |
| 5,202,173 A | 4/1993 | Wu et al. |
| 5,207,663 A | 5/1993 | McQueen |
| 5,210,882 A | 5/1993 | Moretz et al. |
| 5,217,447 A | 6/1993 | Gagnon |
| 5,234,423 A | 8/1993 | Alemany et al. |
| 5,254,111 A | 10/1993 | Cancio et al. |
| 5,260,345 A | 11/1993 | Desmarais et al. |
| 5,261,901 A | 11/1993 | Guay |
| 5,269,775 A | 12/1993 | Freeland et al. |
| 5,296,184 A | 3/1994 | Wu et al. |
| 5,306,267 A | 4/1994 | Hahn et al. |
| 5,342,338 A | 8/1994 | Roe |
| 5,354,597 A | 10/1994 | Capik et al. |
| 5,368,584 A | 11/1994 | Clear et al. |
| 5,368,585 A | 11/1994 | Dokken |
| 5,387,207 A | 2/1995 | Dyer et al. |
| 5,401,266 A | 3/1995 | Runeman et al. |
| 5,405,342 A | 4/1995 | Roessler et al. |
| 5,415,650 A | 5/1995 | Sigl |
| 5,435,014 A | 7/1995 | Moretz et al. |
| 5,451,217 A * | 9/1995 | Fujioka et al. ................ 604/378 |
| 5,458,591 A | 10/1995 | Roessler et al. |
| 5,476,457 A | 12/1995 | Roessler et al. |
| 5,514,121 A | 5/1996 | Roe et al. |
| 5,518,801 A | 5/1996 | Chappell et al. |
| 5,554,142 A | 9/1996 | Dreier et al. |
| 5,562,648 A | 10/1996 | Peterson |
| 5,571,096 A | 11/1996 | Dobrin et al. |
| 5,607,760 A | 3/1997 | Roe |
| 5,609,587 A | 3/1997 | Roe |
| 5,613,959 A | 3/1997 | Roessler et al. |
| 5,620,431 A * | 4/1997 | LeMahieu et al. ....... 604/385.25 |
| 5,624,425 A | 4/1997 | Gray et al. |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,667,503 A | 9/1997 | Roe et al. |
| 5,671,615 A | 9/1997 | Kjærgaard et al. |
| 5,716,349 A | 2/1998 | Taylor et al. |
| H1732 H | 6/1998 | Johnson |
| 5,769,838 A | 6/1998 | Buell et al. |
| 5,772,649 A | 6/1998 | Siudzinski |
| 5,776,121 A | 7/1998 | Roe et al. |
| 5,795,347 A | 8/1998 | Roe et al. |
| 5,814,037 A | 9/1998 | Coates |
| 5,827,261 A | 10/1998 | Osborn et al. |
| 5,843,065 A | 12/1998 | Wyant |
| 5,843,267 A | 12/1998 | Cashaw et al. |
| H1788 H | 2/1999 | Christon et al. |
| 5,865,823 A | 2/1999 | Curro |
| 5,906,603 A | 5/1999 | Roe et al. |
| 5,911,713 A | 6/1999 | Yamada et al. |
| 5,938,648 A | 8/1999 | Lavon et al. |
| 5,941,864 A | 8/1999 | Roe |
| 5,947,946 A | 9/1999 | Fisher et al. |
| 5,968,025 A | 10/1999 | Roe et al. |
| 6,007,528 A | 12/1999 | Osborn |

(56) References Cited

U.S. PATENT DOCUMENTS

| | | |
|---|---|---|
| 6,010,491 A | 1/2000 | Roe et al. |
| 6,061,839 A | 5/2000 | Smolik |
| 6,120,487 A | 9/2000 | Ashton |
| 6,142,983 A | 11/2000 | Suprise et al. |
| 6,193,702 B1 | 2/2001 | Spencer |
| 6,207,738 B1 | 3/2001 | Zuckerman et al. |
| 6,229,061 B1 | 5/2001 | Draggo et al. |
| 6,251,097 B1 | 6/2001 | Kline et al. |
| 6,258,308 B1 | 7/2001 | Brady et al. |
| 6,278,037 B1 | 8/2001 | Schmidt et al. |
| 6,287,169 B1 | 9/2001 | Willms et al. |
| 6,291,039 B1 | 9/2001 | Combe et al. |
| 6,307,119 B1 | 10/2001 | Cammarota et al. |
| 6,316,687 B1 * | 11/2001 | Davis et al. .................. 604/372 |
| H2011 H * | 1/2002 | Freiburger et al. ........... 604/381 |
| 6,368,444 B1 | 4/2002 | Jameson et al. |
| 6,393,621 B1 | 5/2002 | Redwine et al. |
| 6,414,215 B1 | 7/2002 | Roe |
| 6,420,627 B1 | 7/2002 | Ohnishi et al. |
| 6,423,043 B1 | 7/2002 | Gustafsson |
| 6,432,098 B1 | 8/2002 | Kline et al. |
| 6,468,257 B1 | 10/2002 | Ono et al. |
| 6,482,191 B1 | 11/2002 | Roe et al. |
| 6,514,362 B1 | 2/2003 | Zuckerman et al. |
| 6,540,730 B1 | 4/2003 | Niedermeyer |
| 6,547,773 B2 | 4/2003 | Kleinschmidt et al. |
| 6,547,774 B2 | 4/2003 | Ono et al. |
| 6,562,016 B2 | 5/2003 | Shinkai |
| 6,575,951 B1 | 6/2003 | Ono et al. |
| 6,579,273 B2 | 6/2003 | Dupuy |
| 6,605,071 B1 | 8/2003 | Gray et al. |
| 6,613,034 B2 | 9/2003 | Nozaki et al. |
| 6,623,466 B1 | 9/2003 | Richardson |
| 6,669,618 B2 | 12/2003 | Reising et al. |
| 6,680,422 B2 | 1/2004 | Roe |
| 6,716,441 B1 | 4/2004 | Osborne et al. |
| 6,764,477 B1 | 7/2004 | Chen et al. |
| 6,764,478 B2 | 7/2004 | Ashton et al. |
| 6,766,817 B2 | 7/2004 | da Silva |
| 6,786,895 B1 | 9/2004 | Schmitz |
| 6,794,023 B1 | 9/2004 | Melik et al. |
| 6,807,685 B1 | 10/2004 | Hasegawa et al. |
| 6,811,643 B2 | 11/2004 | McAmish et al. |
| 6,817,992 B1 | 11/2004 | Sassak et al. |
| 6,821,612 B1 | 11/2004 | Melik et al. |
| 6,843,949 B2 | 1/2005 | Brady et al. |
| 6,878,647 B1 | 4/2005 | Rezai et al. |
| 6,884,494 B1 | 4/2005 | Curro et al. |
| 6,890,872 B2 | 5/2005 | Bond et al. |
| 6,893,388 B2 | 5/2005 | Reising et al. |
| 6,905,987 B2 | 6/2005 | Noda et al. |
| 6,964,720 B2 | 11/2005 | Schneider et al. |
| 6,980,872 B2 | 12/2005 | Kano et al. |
| 7,000,260 B2 | 2/2006 | Rajala et al. |
| 7,037,569 B2 | 5/2006 | Curro et al. |
| 7,060,149 B2 | 6/2006 | Ortega et al. |
| 7,101,359 B2 | 9/2006 | Kline et al. |
| 7,122,024 B2 | 10/2006 | Nakajima et al. |
| 7,166,095 B1 | 1/2007 | Coates |
| 7,211,531 B2 | 5/2007 | Schneider |
| 7,223,818 B2 | 5/2007 | Autran et al. |
| 7,250,549 B2 | 7/2007 | Richlen et al. |
| 7,264,615 B2 | 9/2007 | Sherrod et al. |
| 7,285,255 B2 | 10/2007 | Kadlec et al. |
| 39,508 A1 * | 1/2008 | Melander ............................ 2/69 |
| 7,344,526 B2 | 3/2008 | Yang et al. |
| 7,387,620 B2 | 6/2008 | Watanabe et al. |
| 7,407,468 B2 | 8/2008 | Reising et al. |
| 7,458,961 B2 | 12/2008 | Carstens |
| 7,462,173 B2 | 12/2008 | Carstens |
| 7,481,801 B2 | 1/2009 | Carstens |
| 7,491,196 B2 | 2/2009 | Frank et al. |
| 7,521,587 B2 | 4/2009 | Busam et al. |
| 7,537,587 B2 | 5/2009 | Carstens |
| 7,576,019 B2 | 8/2009 | Bond et al. |
| 7,626,073 B2 | 12/2009 | Catalan |
| 7,629,501 B2 | 12/2009 | Labit et al. |
| 7,666,175 B2 | 2/2010 | Trennepohl |
| 7,695,463 B2 | 4/2010 | LaVon et al. |
| 7,771,406 B2 | 8/2010 | Mueller et al. |
| 7,771,408 B2 | 8/2010 | Mueller et al. |
| 7,776,771 B2 | 8/2010 | Autran et al. |
| 7,785,309 B2 | 8/2010 | Van Gompel et al. |
| 7,820,875 B2 | 10/2010 | Roe et al. |
| 7,833,211 B2 | 11/2010 | Mansfield |
| 7,914,507 B1 | 3/2011 | Magee |
| 7,993,322 B2 | 8/2011 | Brud et al. |
| 8,118,801 B2 | 2/2012 | Macura et al. |
| 8,158,043 B2 | 4/2012 | Gibson et al. |
| 2001/0031954 A1 * | 10/2001 | Jordan et al. ............. 604/385.01 |
| 2002/0010452 A1 | 1/2002 | Dupuy |
| 2002/0035747 A1 | 3/2002 | Kusibojoska et al. |
| 2003/0091807 A1 | 5/2003 | Desai et al. |
| 2003/0114805 A1 | 6/2003 | Rainville et al. |
| 2003/0125701 A1 | 7/2003 | Widlund |
| 2003/0163104 A1 | 8/2003 | Tears et al. |
| 2003/0233082 A1 | 12/2003 | Kline et al. |
| 2004/0023771 A1 | 2/2004 | Reising et al. |
| 2004/0127867 A1 | 7/2004 | Odorzynski et al. |
| 2004/0127881 A1 * | 7/2004 | Stevens et al. ........... 604/385.22 |
| 2005/0033258 A1 | 2/2005 | Suzuki et al. |
| 2005/0096624 A1 | 5/2005 | Hoshino et al. |
| 2005/0148974 A1 | 7/2005 | Datta et al. |
| 2005/0164587 A1 | 7/2005 | Melik et al. |
| 2005/0177123 A1 | 8/2005 | Catalan |
| 2005/0215965 A1 | 9/2005 | Schmidt et al. |
| 2005/0215968 A1 | 9/2005 | Henderson |
| 2005/0215970 A1 | 9/2005 | Kline et al. |
| 2005/0215971 A1 | 9/2005 | Roe et al. |
| 2005/0234411 A1 | 10/2005 | Ashton et al. |
| 2006/0035055 A1 | 2/2006 | Schneider et al. |
| 2006/0047260 A1 | 3/2006 | Ashton et al. |
| 2006/0058766 A1 | 3/2006 | Mueller et al. |
| 2006/0069372 A1 | 3/2006 | Chakavarty et al. |
| 2006/0087053 A1 | 4/2006 | O'Donnell et al. |
| 2006/0107505 A1 | 5/2006 | Desai et al. |
| 2006/0129114 A1 | 6/2006 | Mason et al. |
| 2006/0129116 A1 | 6/2006 | Hughes et al. |
| 2006/0178652 A1 | 8/2006 | Miller |
| 2006/0189956 A1 | 8/2006 | Catalan |
| 2006/0229582 A1 | 10/2006 | LaVon |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2006/0264885 A1 | 11/2006 | Carstens |
| 2006/0282056 A1 | 12/2006 | McDonald |
| 2006/0293637 A1 | 12/2006 | La Von et al. |
| 2007/0005038 A1 | 1/2007 | Mansfield et al. |
| 2007/0032772 A1 | 2/2007 | Ehrnsperger et al. |
| 2007/0142798 A1 | 6/2007 | Goodlander et al. |
| 2007/0142816 A1 | 6/2007 | Carstens |
| 2007/0191806 A1 | 8/2007 | Mueller et al. |
| 2007/0203301 A1 | 8/2007 | Autran et al. |
| 2007/0239130 A1 | 10/2007 | Trennepohl |
| 2007/0249254 A1 | 10/2007 | Mansfield |
| 2007/0287348 A1 | 12/2007 | Autran et al. |
| 2007/0287982 A1 | 12/2007 | Lodge et al. |
| 2007/0287983 A1 | 12/2007 | Lodge et al. |
| 2007/0293111 A1 | 12/2007 | Mansfield |
| 2008/0004582 A1 | 1/2008 | Lodge et al. |

(56) References Cited

U.S. PATENT DOCUMENTS

| | | |
|---|---|---|
| 2008/0004583 A1 | 1/2008 | Desai et al. |
| 2008/0004584 A1 | 1/2008 | Langdon et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0009817 A1 | 1/2008 | Norrby |
| 2008/0015537 A1 | 1/2008 | Lodge et al. |
| 2008/0033388 A1 | 2/2008 | Muellerg et al. |
| 2008/0045917 A1 | 2/2008 | Autran et al. |
| 2008/0114320 A1 | 5/2008 | Beck et al. |
| 2008/0114327 A1 | 5/2008 | Barge |
| 2008/0119813 A1 | 5/2008 | Carstens |
| 2008/0119814 A1 | 5/2008 | Carstens |
| 2008/0119816 A1 | 5/2008 | Carstens |
| 2008/0125739 A1 | 5/2008 | Lodge et al. |
| 2008/0183148 A1 | 7/2008 | Labit et al. |
| 2008/0188822 A1 | 8/2008 | Lodge et al. |
| 2008/0224351 A1 | 9/2008 | Curro et al. |
| 2008/0275412 A1* | 11/2008 | Molander et al. ............. 604/370 |
| 2008/0287983 A1 | 11/2008 | Smith et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312628 A1 | 12/2008 | Hundorf et al. |
| 2008/0319407 A1 | 12/2008 | Erdem et al. |
| 2009/0038738 A1 | 2/2009 | Nakamura |
| 2009/0048571 A1 | 2/2009 | Spitzmueller et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0088713 A1 | 4/2009 | Norrby |
| 2009/0127742 A1 | 5/2009 | Qureshi et al. |
| 2010/0005570 A1 | 1/2010 | Rachman |
| 2010/0179495 A1* | 7/2010 | Roe ............................. 604/367 |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe |
| 2010/0201024 A1 | 8/2010 | Gibson et al. |
| 2011/0009843 A1* | 1/2011 | Krook ....................... 604/385.01 |
| 2011/0046590 A1* | 2/2011 | Mukai et al. ................. 604/367 |
| 2011/0172628 A1 | 7/2011 | Roe et al. |
| 2011/0288515 A1* | 11/2011 | Roe et al. ................ 604/385.03 |
| 2011/0313388 A1* | 12/2011 | Gabrielii et al. ......... 604/385.24 |
| 2012/0022481 A1* | 1/2012 | Roe et al. ...................... 604/378 |
| 2012/0049404 A1 | 3/2012 | Gibson et al. |
| 2012/0179126 A1* | 7/2012 | Kanya et al. ................. 604/366 |
| 2012/0302985 A1* | 11/2012 | Mukai et al. ............. 604/385.24 |

FOREIGN PATENT DOCUMENTS

| | | |
|---|---|---|
| CA | 2 221 209 | 11/1996 |
| CA | 2 365 577 | 6/2003 |
| CI | 1505531 A | 6/2004 |
| CN | 1505531 A | 6/2004 |
| CN | 1285727 A | 11/2006 |
| DE | 103 03 903 | 11/2003 |
| EP | 0 023 804 | 2/1981 |
| EP | 0 187 726 | 7/1986 |
| EP | 0 319 314 | 6/1989 |
| EP | 0 811 362 A1 | 12/1997 |
| EP | 0 549 988 | 6/1998 |
| EP | 0 796 069 | 8/2000 |
| EP | 0 763 353 | 6/2002 |
| EP | 2 106 775 | 10/2009 |
| FR | 2532337 A1 | 3/1984 |
| FR | 2606257 A1 | 5/1988 |
| GB | 0 112 638 A | 1/1918 |
| GB | 112638 A | 1/1918 |
| GB | 2 440 314 | 1/2008 |
| JP | 55-37849 U | 9/1978 |
| JP | 57-138908 | 8/1982 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 61-168103 U | 10/1986 |
| JP | 62-110903 | 7/1987 |
| JP | 63-196701 A | 8/1988 |
| JP | 03-091325 | 1/1990 |
| JP | 04-77922 | 11/1990 |
| JP | 06-178795 | 1/1993 |
| JP | 6-63077 A | 3/1994 |
| JP | 30-73695 | 9/2000 |
| JP | 3073695 | 9/2000 |
| JP | 2001/353183 A1 | 12/2001 |
| JP | 2001-353183 A1 | 12/2001 |
| JP | 2002-95698 A | 4/2002 |
| JP | 2002-325786 | 11/2002 |
| JP | 2003-038564 | 2/2003 |
| JP | 2003-190213 A | 7/2003 |
| JP | 2005-6827 | 1/2005 |
| JP | 2005-111119 | 4/2005 |
| JP | 31-09189 | 5/2005 |
| JP | 2007-244506 | 3/2006 |
| JP | 2007-68654 A | 3/2007 |
| JP | 2008-055002 A | 3/2008 |
| WO | WO 90/08524 | 8/1990 |
| WO | WO 91/16871 | 11/1991 |
| WO | WO 92/01431 | 2/1992 |
| WO | WO 92/15444 | 9/1992 |
| WO | WO 94/15663 | 7/1994 |
| WO | WO 95/10992 | 4/1995 |
| WO | WO 95/16746 | 6/1995 |
| WO | WO 96/17572 | 6/1996 |
| WO | WO 96/24319 | 8/1996 |
| WO | WO 96/32912 | 10/1996 |
| WO | WO 00/65348 | 11/2000 |
| WO | WO 01/34080 | 5/2001 |
| WO | WO 02/066086 | 8/2002 |
| WO | WO 2004/060229 | 7/2004 |
| WO | WO 2005/039469 | 5/2005 |
| WO | WO 2005/052052 | 6/2005 |
| WO | WO 2005/096855 | 10/2005 |
| WO | WO 2005/097031 | 10/2005 |
| WO | WO 2008/030984 | 3/2008 |
| WO | WO 2008/120959 | 10/2008 |
| WO | WO 2008/142634 | 11/2008 |
| WO | WO 2010/053006 | 5/2010 |
| WO | WO 2010/111717 | 9/2010 |
| WO | WO 2010/113071 | 10/2010 |
| WO | WO 2010/134169 | 11/2010 |
| WO | WO 2010/135510 | 11/2010 |
| WO | WO 2011/047252 | 4/2011 |
| WO | WO 2011/047264 | 4/2011 |

OTHER PUBLICATIONS www.fuzzibunz.com—Web pages dated Nov. 23, 2009.

(56) References Cited

OTHER PUBLICATIONS www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.
Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7, 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).
"Y2K Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), The Changes in Cloth Diapers Have Made Them all the Rage. Learning the Lingo Navigating Cloth" Omaha World Herald (Mar. 22, 2004).
37 photographs (obtained from Marketing Technology Service, Inc.) of a product believed to be a product of Kao Corp. and sold in Japan in 1986 (translations provided by Applicants.
Data Sheet, p. V-17, from "Baby Diaper Design Update—1987", publication of Marketing Technology Service, Inc., product believed to be a product of Kao Corp. sold in Japan in 1986 or 1987.
US 5,583,910, 02/1994, Flint (withdrawn).
International Search Report dated Jun. 8, 2010, 7 pages.
E-mail from Elson Silva, dtd Jul. 26, 2010, re: Respecting Hydrology Science.
All Office Actions, U.S. Appl. No. 12/687,412.
All Office Actions, U.S. Appl. No. 12/687,425.

* cited by examiner

REUSABLE OUTER COVER FOR AN ABSORBENT ARTICLE HAVING ZONES OF VARYING PROPERTIES

FIELD OF THE INVENTION

This disclosure relates generally to absorbent articles, such as diapers, training pants, adult incontinence devices, sanitary napkins, and the like, and more specifically, to a reusable outer cover for an absorbent article, the outer cover having zones of varying properties.

BACKGROUND OF THE INVENTION

Reusable absorbent articles have traditionally involved an absorbent insert, such as a cloth diaper, and a leak-resistant outer cover, usually including a heavy polymer film formed to resemble underwear. More recently, absorbent articles have become available with a reusable outer cover and disposable inserts. After the disposable insert is soiled, it is discarded, and a new disposable insert is placed in the outer cover, which may be cleaned or otherwise reconditioned prior to reuse. Additionally, new outer covers have become available which offer one or more benefits over past outer covers. Some of the newer outer covers may use non-traditional materials or constructions to make the outer cover more comfortable (softer, more flexible/more conforming to the wearer), more breathable, and/or more aesthetically pleasing. Moreover, many of the newer outer covers achieve these benefits at the expense of other desirable attributes of a reusable outer cover. For example, enhanced breathability may come with lower leakage protection, and softer materials may be less durable over multiple use cycles.

There remains a need for a reusable outer cover that can provide competing or even contradictory properties to improve containment, wearer comfort, skin condition, and aesthetic appeal.

SUMMARY OF THE INVENTION

What is claimed is a reusable outer cover for an absorbent article. The reusable outer cover may comprise a front zone and a rear zone, wherein the rear zone has a greater percent extension than the front zone in the Whole Product Back Extension test. The rear zone may extend at least 50% under an applied force of 5N and may have an unload force of at least 1.0N at 25% extension. The front zone may extend at least 15% under an applied force of 5N.

The reusable outer cover may comprise a front zone, a crotch zone, and, a rear zone. The crotch zone may have a higher WVTR than the front and rear zones. The crotch zone may have a WVTR of at least 1200 g/m²/24 hrs, or at least 3000 g/m²/24 hrs. The crotch zone may have a higher fluid penetration resistance than the front and rear zones. The crotch zone may have a fluid penetration resistance of at least 5 mbar.

The crotch zone may have a wearer-facing surface comprising a first layer and a garment-facing surface comprising a second layer, and the second layer may be more hydrophobic than the first layer. The second layer may be more hydrophobic than the front and rear zones.

The reusable outer cover may comprise a side zone, a rear zone, a front zone, and a crotch zone. The side, rear, and front zones may have a higher static coefficient of friction relative to skin than the crotch zone. The side, rear, and front zones may have a static coefficient of friction relative to skin greater than 0.5. The crotch zone may have a static coefficient of friction relative to skin less than 0.4. The side zone may have a higher static coefficient of friction relative to skin than the front and rear zones. The side zone may have a static coefficient of friction relative to skin greater than 0.3.

The reusable outer cover may comprise an absorbent insert removably situated against at least a portion of the crotch zone, and the crotch zone may have a higher static coefficient of friction relative to the absorbent insert than the side, rear, and front zones.

DETAILED DESCRIPTION OF THE INVENTION

The term "absorbent article" as used herein refers to devices which absorb and contain body exudates and, more specifically, refers to devices which are placed against or in proximity to the body of the wearer to absorb and contain various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as sanitary napkins and panty liners, and the like. Absorbent articles include reusable absorbent articles.

The term "disposable," as used herein in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

The term "reusable," as used herein means that a referenced material, component, or all of an absorbent article is configured to be restored and/or reused for more than one usage cycle (e.g., a diaper change). In some reusable absorbent articles, part, or parts, or substantially all, or all of the articles may be launderable or laundering resistant, as defined and described herein. Another part or parts of a reusable absorbent article may not be launderable or laundering resistant. For example, some parts of a reusable absorbent article may be discarded after soiling and replaced with a new part, such as an absorbent insert which is used with a reusable outer cover.

The term "launderable," as used herein means that a referenced material, component, or all of an absorbent article is configured to withstand a large number (e.g. at least 10, in some embodiments up to 50, in other embodiments more than 50) of cycles of machine washing and machine drying (as defined by AATCC Test Method 124-2001, with modifications as described below), without significant degradation to the appearance or performance of the article that would render it unsuitable for its intended functionality or use. Since hand-washing and line-drying are typically less stressful on an absorbent article than machine washing and machine drying, it is expected that a material, component, or article that is machine washable and machine dryable should also be hand-washable and hand-dryable for at least as many cycles. As an example, a reusable absorbent article may include an outer cover that is launderable. Launderable articles are designed to be suitable for use after many washings, similar to types of clothing.

The term "laundering resistant," as used herein means that a referenced material, or component, or all of an absorbent article is configured to withstand a small number (e.g. at least one, in some embodiments up to five, in other embodiments more than five) of cycles of machine washing and machine drying (as defined by AATCC Test Method 124-2001, with modifications as described below), without significant degradation to the appearance or performance of the article that would render it unsuitable for its intended functionality and/or use. As an example, a reusable absorbent article may include an outer cover that is laundering resistant. Laundering resistant articles generally experience degradation after fewer laundering cycles than launderable articles.

The term "absorbent insert," as used herein refers to a component of an absorbent article used to capture or contain body exudates, and which is removably associated with the absorbent article during use. For example, an absorbent insert may be press-fit into place, or may be releasably attached to some portion of the absorbent article, as by mechanical fasteners, adhesives, cohesives, and the like. An absorbent insert may be disposable or reusable.

The term "wearer-facing," as used herein means the side of an article or component of an article that is nearest the wearer when the article is fitted to a wearer as intended for normal use. The term "garment-facing," as used herein means the side of an article or component of an article that is opposite to the wearer-facing surface and furthest from the wearer when the article is fitted to a wearer as intended for normal use.

As used herein, the terms "inboard" and "outboard" refer to the position of an object relative to the longitudinal or lateral centerline of an absorbent article. A first object is inboard of a second object if the first object is nearer the longitudinal or lateral centerline than the second object. A first object is outboard of a second object if the first object is farther from the longitudinal or lateral centerline than the second object.

As used herein, the term "zone" refers to a defined, macroscopic area of an outer cover having at least one shared property or function across the defined area. A zone of an outer cover may refer to all of the components in the outer cover in the zone, or only a specified portion of the components of the outer cover in the zone. For example, a zone may be limited to one surface of the defined area of an outer cover, or may refer to multiple layers or multiple layered components within the defined area making up the zone.

As used herein, the term "hydrophilic" describes surfaces which are wettable by aqueous fluids (e.g., aqueous body fluids) deposited on these surfaces. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A surface is said to be wetted by a fluid (i.e., hydrophilic) when either the contact angle between the fluid and the surface, is less than 90°, or when the fluid tends to spread spontaneously across the surface, both conditions normally co-existing. Conversely, a surface is considered to be "hydrophobic" if the contact angle is greater than 90° and the fluid does not spread spontaneously across the surface of the fiber. Contact angle is measured using a Kruss Drop Shape Analysis System, Model DSA10-Mk2, as available from Kruss USA in Charlotte, N.C.

In order to enhance functional properties such as fit, wearer comfort, containment, skin condition and appearance of outer cover 10, it may be desirable to fashion outer cover 10 to include zones of different properties to accommodate anatomical contours and body movements of the intended wearer, as well as the anatomic regions associated with bodily exudate release from the body. Human anatomy in the lower torso/hip/thigh region is asymmetric about the lateral plane of the body, i.e., the geometry of the front of the human body is different than that of the back. Additionally, articulation of the waist and legs via their respective joint and skeletal structures is asymmetric about the lateral pane of the wearer, e.g., the torso bends preferentially toward the front of the wearer. Accordingly, different properties, such as different stretch characteristics, may be desired in different portions of an absorbent article. An outer cover for an absorbent article, for example, may include two or more zones having different values for various functional properties, such as extensibility and/or elastic stretch, elastic recovery or unload force, breathability, fluid penetration resistance or hydrohead, hydrophilicity/hydrophobicity, and coefficient of friction.

General Structure of an Absorbent Article

Figure 1:
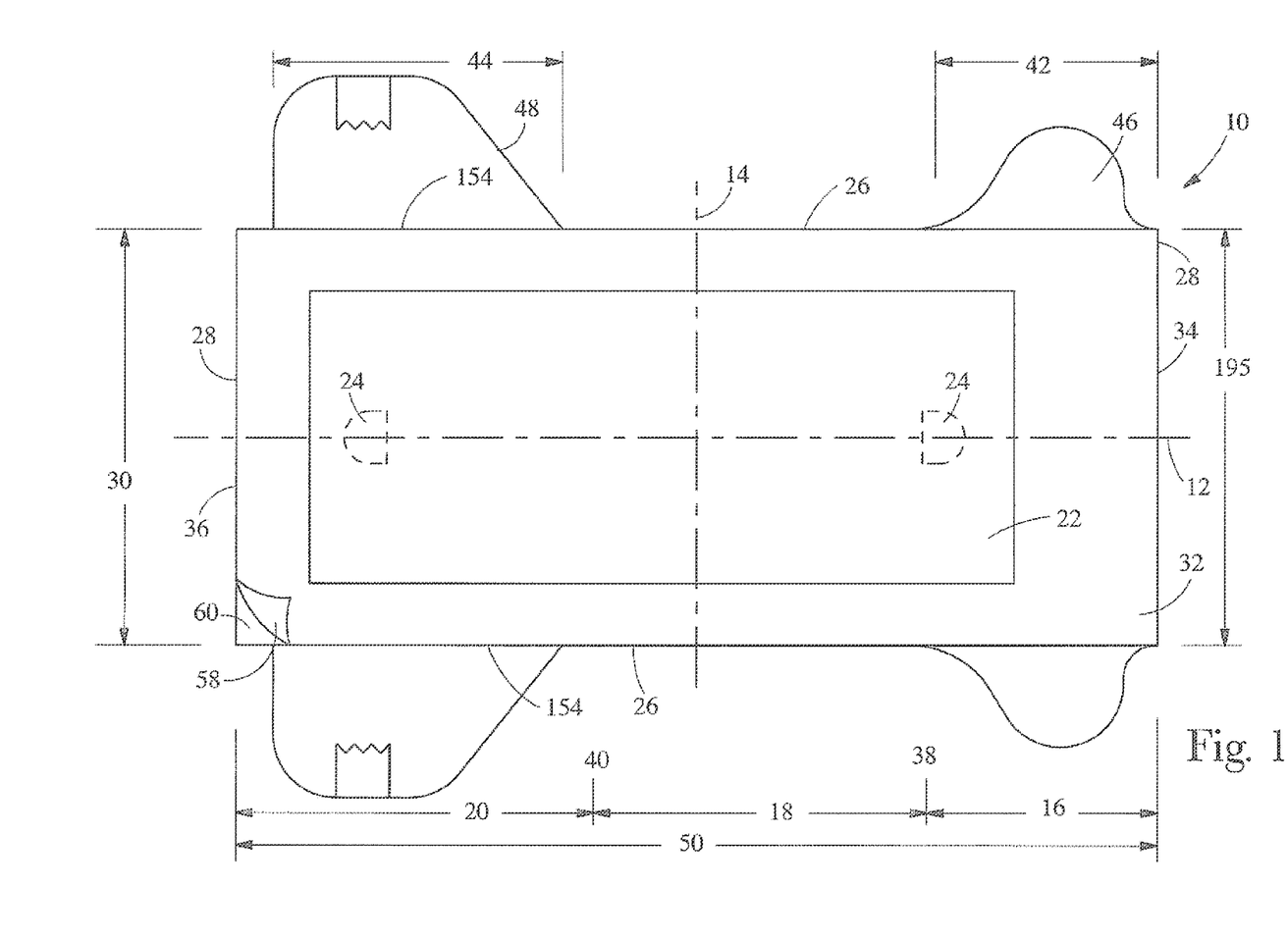
FIG. 1. is a plan view of an exemplary reusable outer cover.
Figure 2:
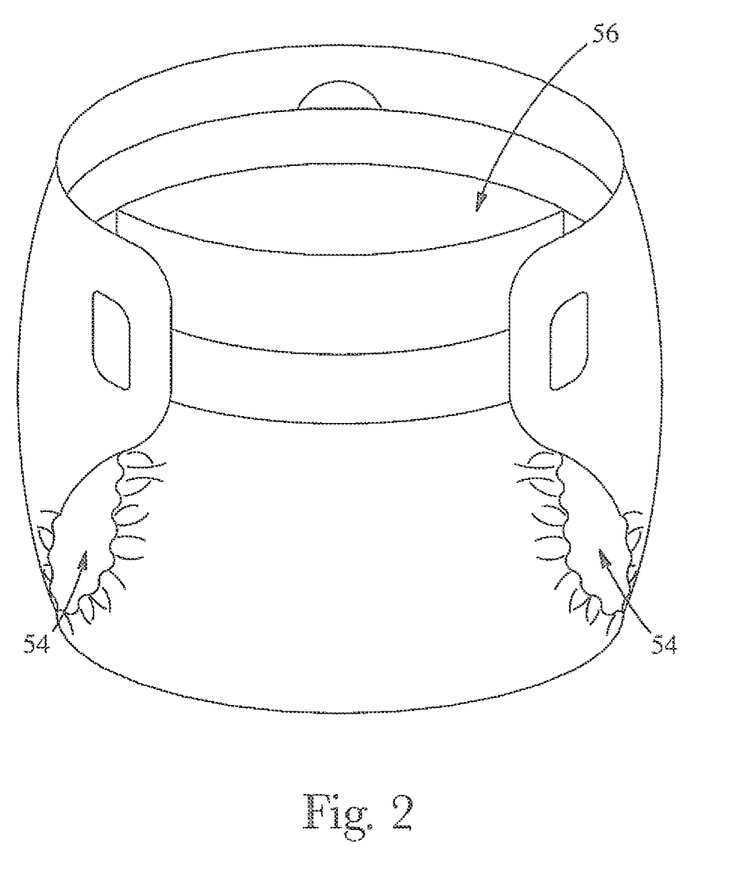
FIG. 2 is a perspective view of an exemplary reusable outer cover configured for wearing.

As shown in FIG. 1, exemplary absorbent article 10 has outer cover 32. Outer cover 32 may have longitudinal axis 12 and lateral axis 14 perpendicular to longitudinal axis 12. Outer cover 32 has front region 16, back region 20, and crotch region 18 disposed longitudinally between front region 16 and back region 20. Crotch region 18 of outer cover 32 is the rectangle, defined below, that is centered longitudinally and laterally about the article's crotch point. The crotch point is determined by placing absorbent article 10 on a wearer in a standing position and then placing an extensible filament around the legs in a figure eight configuration. The point in the article corresponding to the point of intersection of the filament is deemed to be the crotch point of the article. It should be understood that the crotch point is determined by placing the absorbent article on a wearer in the intended manner and determining where the crossed filament would contact the article.

With regard to sanitary napkins and pantiliners, the length of crotch region 18 corresponds to approximately 60 to 100% of the outer cover's total length 50, generally about 80% of the outer cover's total length 50. With regard to incontinence devices (e.g., diapers, adult incontinent articles) and other absorbent articles, the length of crotch region 18 corresponds to approximately 40 to 80% of the outer cover's total length 50 (i.e., in the y-dimension), generally about 60% of the outer cover's total length 50. The width of crotch region 18 is equivalent to the width 30 of outer cover 32 of absorbent article 10 as measured at the crotch point. By way of illustration, for an incontinent article outer cover having a length of 20 in. and a width at the crotch point of 4 in., the crotch region is the rectangle, centered on the crotch point, having a length of 12 in. and a width of 4 in.

Absorbent insert 22 may be attached at attachment points 24 and serves to capture or contain body exudates, such as urine, feces, menses, perspiration, etc. As shown, absorbent insert 22 is attached to outer cover 32; however, absorbent insert 22 may be attached to any component of absorbent article 10, or to an intermediate layer other than outer cover 32, if present. Two attachment points 24 are shown proximate the longitudinal ends of absorbent insert 22, however, absorbent insert 22 may be attached at any number, shape, or pattern of attachment points suitable for keeping absorbent insert 22 in its intended position, for example, proximate the anatomical source of body exudates, during use. In some embodiments, absorbent insert 22 may be held in place primarily or exclusively by an outer cover zone having a high coefficient of friction, as described below, in which embodiments there may be no distinct attachment point 24, or, rather, there may be one relatively large attachment point 24. In some embodiments, absorbent article 10 has an integral absorbent core, and may or may not be attached to removable absorbent insert 22 for supplemental absorbency. Absorbent insert 22 may be shaped to provide improved wearer comfort and aesthetics. For example, absorbent insert 22 may have a generally hourglass shape to provide improved fit between and around the wearer's legs.

Outer cover 32 has laterally opposed longitudinally extending edges 26 and longitudinally opposed laterally extending edges 28. Longitudinally extending edges 26 and laterally extending edges 28 are shown as straight lines, however, longitudinally extending edges 26 and laterally extending edges 28 may be contoured. For example, longitudinally extending edges 26 may be shaped to more comfortably accommodate the wearer's legs, and laterally extending edges 28 may be shaped to more comfortably accommodate the wearer's stomach, hips or back. In the specific case of an infant diaper, laterally extending edge 28 may have a shaped profile in the front region to accommodate an umbilical cord stump. Other contours are possible. In FIG. 1, width 30 of outer cover 32 at the crotch point is roughly the same as width 195 between longitudinally extending edges 26 at the rear waist, however, in embodiments having longitudinally extending edges 26 which are contoured, these widths may differ.

Outer cover 32 has a front zone, extending laterally between longitudinally extending edges 26 of outer cover 32 and longitudinally between front waist edge 34 and front edge 38 of crotch region 18. Outer cover 32 has a rear zone, extending laterally between longitudinally extending edges 26 of outer cover 32, and longitudinally between rear waist edge 36 and rear edge 40 of crotch region 18. Outer cover 32 has a crotch zone, extending laterally between longitudinally extending edges 26 of outer cover 32, and longitudinally between front edge 38 and rear edge 40 of crotch region 18. Outer cover 32 has a side zone, extending laterally around the entire waist circumference when absorbent article 10 is fitted to a wearer. That is, the side zone encompasses two full widths of outer cover 32, including the side panels, if present, on each side. The side zone extends longitudinally a distance equal to length 42 of front side panel 46 or length 44 of rear side panel 48, whichever is greater. If there are no side panels, the side zone extends longitudinally a distance equal to the length of the front zone in front region 16 and a distance equal to the length of the rear zone in back region 20.

Outer cover 32 has a waist zone extending laterally along the entire width of front waist edge 34 and rear waist edge 36, inclusive of the width of front side panels 46 and rear side panels 48, if present. The waist zone extends longitudinally approximately 5 to 15% of length 50 of outer cover 32 inboard of each of front waist edge 34 and rear waist edge 36. For example, the waist zone may extend longitudinally about 10% of length 50 of outer cover 32 inboard of each of front waist edge 34 and rear waist edge 36. Outer cover 32 has a front waist zone extending laterally along the entire width of front waist edge 34, inclusive of the width of front side panels 46, if present. The front waist zone extends longitudinally approximately 5 to 15% of length 50 of outer cover 32 inboard of front waist edge 34. For example, the front waist zone may extend longitudinally about 10% of length 50 of outer cover 32 inboard of front waist edge 34. Outer cover 32 has a rear waist zone extending laterally along the entire width of rear waist edge 36, inclusive of the width of rear side panels 48, if present. The rear waist zone extends longitudinally approximately 5 to 15% of length 50 of outer cover 32 inboard of rear waist edge 36. For example, the rear waist zone may extend longitudinally about 10% of length 50 of outer cover 32 inboard of rear waist edge 36.

Outer cover 32 has two leg zones adjacent each longitudinally extending side edge 26, extending laterally from each longitudinally extending side edge approximately 10-25% of width 30 of outer cover 32 at the crotch point, and extending longitudinally along width 30 of outer cover 32. For example, the leg zones may extend longitudinally about 15% of width 30 of outer cover 32. Outer cover 32 has an ear zone which includes all portions of outer cover 32 which extend laterally outboard from longitudinally extending side edges 26 (e.g., encompassing the side panels, if present).

Stretch Zones

Certain regions of outer cover 32 may require more extensibility and/or elastic recovery than other regions in order to accommodate variation in wearer geometry, movement of the wearer during use, or both of these. For example, the wearer's buttocks region can expand about 50% in the lateral direction as the wearer moves from a standing position to a sitting or squatting position. Additionally, within a given weight range, the various dimensions of a wearer, such as waist circumference, thigh circumference, rise through the crotch, etc., may vary significantly. To provide for better fit, comfort, and ease of application, the stretch properties of the outer cover may be different in different regions to accommodate these variations. Increased lateral extensibility or elastic elongation in the rear region of the outer cover as compared to the front region of the outer cover may serve to better conform to and cover the buttocks through movements or body positions of the wearer (including sitting and/or bending forward at the hips). For example the back waist region of the outer cover may include a zone which extends at least about 15%, or at least about 20%, under an applied force of 5N in the Whole Product Back Extension test described below. Greater extension may allow the outer cover to accommodate a wider range of wearer shapes, sizes, and motions. In order to provide a conforming fit in all wearer body positions, the outer cover material—that is, the material or materials from which the outer cover is made—may extend 50% in the lateral direction under no more than 10 N, and more preferably 5 N, of applied force to accommodate buttocks expansion during wearing.

Likewise, a zone of increased longitudinal elongation in rear region 20 of outer cover 32 may serve to better conform to and cover the buttocks region of the wearer as the wearer bends or squats. Also, a zone of lateral elongation at front waist 34 (i.e., increased extension as compared to the crotch region) may allow the outer cover to accommodate wearer abdominal expansion when the wearer is in a seated position. Conversely, since relatively little lateral or longitudinal expansion of the body occurs in the front part of crotch region 18 of outer cover 32, this region may include a zone of lower, or even zero, elongation.

In addition to providing for differences in wearer geometry or motion, outer cover 32 may also provide sustained fit, resisting sagging and irrecoverable downward movement under stresses applied to the article from bodily motion and/or increasing mass of bodily exudates in the article during the wearing period. A minimum magnitude of elastic recovery force may be required in at least certain zones of outer cover 32 to achieve this. For example, the elastic recovery force may be higher in the rear waist 36 of outer cover 32 than in the buttocks region. While the outer cover material in the buttocks region may extend under low forces to accommodate buttocks expansion during bodily movement, the waist region may maintain a minimum level of elastic recovery force to maintain a secure fit and anchoring of the article around the wearer's torso. Outer cover 32 may include a rear waist zone that retains at least about 1.0N, 1.5N, or 2.0N "unload" force at 25% elongation in the Whole Product Back Extension test. A higher unload force may provide improved fit and resistance to sagging. Excessive unload force may contribute to red marking or abrasion of the wearer's skin. The magnitude of force which is excessive will vary with other details of the construction of the outer cover (such as the coefficient of friction between the outer cover material and the skin) and the delicacy of the skin contacted by the outer cover, which may vary between locations on the same user (such as the hip and the perineal area) as well as between different kinds of users (such as incontinent or menstruating adults and infants).

Different elastic properties can be provided in different zones by using different materials in the different zones. In some embodiments, outer cover 32 may be fashioned from a single material that is treated or otherwise altered to manipulate its properties in different zones. For example, an elastically extensible material can be fixed into place at selected locations, as by sewing, gluing, hot-melting, etc., to "deaden" the elastic, thereby locally reducing or even eliminating the elastic properties of the material. Alternately, a single, uniform material that is inelastic until activated can be used, and activated only in the desired zones. Elasticity and elastic recovery can be created or increased by adding elastic fibers, strips, scrims, webs, films or bands to the outer cover material. For example, one or more elastic bands can be laminated into the zones with desired elastic properties. One or more anchoring bands 52 may be used to increase elastic recovery. Anchoring bands are described, for example, in U.S. Provisional Patent Application 61/144,883, filed Jan. 15, 2009. Of course, a combination of these techniques may be used to provide different levels of elasticity in different zones, and even different levels of elasticity in response to different forces (i.e., lateral forces, as from wearer respiration and movement, or longitudinal forces from wearer movement and exudate loading).

Breathability and Skin Condition

Outer cover 32 may, in part due to the localized nature of bodily exudate release associated with human anatomy, contain more urine and/or feces in one region of the article than another. Regions of the article having higher concentrations of bodily exudates often have an associated higher level of humidity between the article and the wearer's skin. Additionally, certain regions of the body covered by the article, e.g., in the intertriginous and genital regions, have a higher concentration of sweat glands, and often experience a higher amount of released sweat. These areas may have increased local humidity as a result. Increased localized humidity near the skin can lead to over-hydration of the skin, which may contribute to erythema, diaper dermatitis, and/or increased susceptibility of the over-hydrated skin to abrasion. Accordingly, outer cover 32 may have at least one zone having a higher breathability in these regions associated with increased humidity. These zones may have a Water Vapor Transmission Rate (WVTR) as measured by the Mocon test described below to allow sufficient water vapor from urine and/or sweat to leave the interior of the article, maintaining the skin hydration at a lower level. For example, outer cover 32 may have a zone having a WVTR of at least about 1200 g/m$^2$/24 hr or 3000 g/m$^2$/24 hr. Higher WVTRs may be helpful when the ambient conditions are higher in temperature and/or humidity, when the wearer is more active (e.g., perspires more), and/or when the diaper has a higher loading of urine or other liquid exudates (e.g., during overnight use or when the user is a "heavy wetter"). Thus, a WVTR of at least about 1200 g/m$^2$/24 hr may indicate a serviceable outer cover in typical use, while a WVTR of at least about 3000 g/m$^2$/24 hr may indicate a serviceable outer cover under more challenging conditions.

In the past, outer covers for reusable absorbent articles have been made of relatively thick films with very low water vapor transmission rates, often well below 1000 g/m$^2$/24 hr. One method of producing an outer cover for a reusable absorbent article with a more robust WVTR is to use a microporous film. However, microporous films exhibit minimal elastic extension and recovery. A breathable, stretchable outer cover may be desirable. For example, a stretchable woven fabric may be used as the outer cover. A porous, stretchable woven fabric allows air and water vapor to pass through. A higher WVTR may also be achieved by mechanically aperturing the outer cover, such that air and water vapor can traverse the thickness of the outer cover. Liquid penetration can then be managed by controlling the aperture or pore size and/or by providing inner layer 58 of outer cover 10, wherein at least one of inner layer 58 and outer layer 60 is hydrophobic. A breathable, stretchable outer cover with reduced liquid penetration may also be provided by employing more than one layer of a stretchable woven fabric as the outer cover. In any of these embodiments, inner layer 58 and outer layer 60 may have the same or similar properties, and provide a higher WVTR by duplication of the barrier. In some embodiments, inner layer 58 and outer layer 60 are different. For example, outer layer 60 may be a soft, extensible layer with pleasant tactile and aesthetic properties, while inner layer 58 is a hydrophobic layer with desirable moisture barrier properties. Alternatively, the outer layer 60 may be more hydrophobic than the inner layer 58. Inner layer 58 may have a greater elastic return force than outer layer 60, such that the pores of inner layer 58 are generally maintained in a smaller, less open configuration, and, therefore, transmit less water.

The WVTR of outer cover 32 may be varied in different zones by using different materials in different zones. If outer cover 32 is made of a single layer, the single layer may be pieced together of different materials. If outer cover 32 is made of more than one layer, the layers may be different materials which are not co-extensive, such that some zones have the breathability of the composite and some zones have the breathability of only one of the layers. The WVTR may also be varied in different zones by using different treatments of the same material or materials in different zones. For example, different zones may have different depths, frequency, or patterns of aperturing, possibly including zones or portions of a zone which are not apertured. Possible treatments include mechanical treatments, such as aperturing, as well as alternate treatments such as exposure to heat, compression or strain, and chemical treatments.

Fluid Penetration Resistance

Certain regions of outer cover 32, either in proximity to the anatomic exudate release points or the perimeter of an absorbent core, assembly, or insert 22, may be more likely to experience contact with urine, feces, or other exudates. Outer cover 32 may include zones of higher fluid penetration resistance in these regions as compared to other regions of outer cover 32 to prevent leakage through outer cover 32 onto the wearer's clothing or other environmental objects. Fluid penetration resistance may be measured by the Mocon hydrohead test, and may vary from 5 mbar to 20-50 mbar or more over the surface of the outer cover. The greater the hydrohead value, the less likely it is that liquid exudates will be able to traverse the material making up the outer cover (as opposed to leaking along the edges of the outer cover, such as the leg openings 54 or waist opening 56).

Fluid penetration resistance may be decreased by aperturing the outer cover, or by mechanically deforming or stretching the outer cover. Fluid penetration resistance may be increased by adding additional layers of the same or different materials, or by treating one or more materials in a laminate. For example, the hydrophobic treatments described below may also increase the fluid penetration resistance of the outer cover material.

Hydrophobicity

As described above, certain regions of outer cover 32 may be more prone to contact with urine, feces, or other exudates. Outer cover 32 may include zones having a greater hydrophobicity in these regions in order to reduce the likelihood of fluid penetration and leakage. Alternatively, outer cover 32 may include zones of greater hydrophilicity, or even absorbent capacity, in these regions in order to control or trap the exudates and prevent them from flowing across outer cover 32 to a perimeter, such as leg openings 54 or waist opening 56, where they may leak into the environment. The zones of different hydrophilicity and/or hydrophobicity may be spaced in the lateral or longitudinal directions in outer cover 32, or may be spaced through the thickness of outer cover 32 (e.g., via different layers). The hydrophobicity (or hydrophilicity) of the outer cover may be measured by determining the contact angle of water with the outer cover material.

Hydrophobicity may be varied by using different materials having different inherent hydrophobicities. For example, part of outer cover 32 may be fashioned from cotton and part of outer cover 32 may be fashioned from a polypropylene film with minimal pores or pinholes. Hydrophobicity may also be varied by selectively coating part of outer cover 32. Hydrophobic treatments are well known, and include, for example, waxes, hydrophobic silicone compositions, proprietary treatments such as Scotchgard™ Protector Repellent and Repel Teflon® Fabric Protector, and the like. Hydrophobicity may also be varied by selectively layering materials, in a bonded, partially bonded, or substantially unbonded laminate. A hydrophobic material may be applied to selected areas of outer cover 32 using any means known in the art, including, but not limited to, spraying, coating, and laminating.

Static Coefficient of friction

Certain regions of outer cover 32 contact regions of the wearer's body, such as the hip, buttock, and upper thigh regions, and may be more capable than other regions of providing anchoring support to outer cover 32. An outer cover having zones of higher static coefficient of friction on the wearer-facing surface 62 in the regions may tend to have increased support and improved sustained fit during the wearing process. Additionally, certain regions of outer cover 32 may contact absorbent insert 22 during wearing, while others may not. Outer cover 32 may have zones of higher static coefficient of friction in at least a portion of this insert contact area, such as crotch region 18 of outer cover 32, to minimize shifting of absorbent insert 22 within outer cover 32 during wear that may lead to poor fit and leakage. Static coefficient of friction may be measured as described below, and may vary from 0.3 to 0.4 or 0.5 or higher over the surface of the outer cover. In some embodiments, the static coefficient of friction may be greater than 0.8 or 1.0.

The static coefficient of friction for a material depends in part on the material against which it is moving. Thus, the same zone may be configured to provide a relatively high static coefficient of friction relative to a first material on a first surface and a relatively low static coefficient of friction relative to a second material on a second surface. For example, it may be desirable to configure crotch region 18 of outer cover 32 such that wearer-facing surface 62 has a relatively high static coefficient of friction relative to absorbent insert 22, and garment-facing surface 64 has a relatively low static coefficient of friction relative to common fabrics (to reduce pilling or other damage to clothing during use) or to skin (to reduce the potential for irritation from incidental contact between the outer cover and the user's skin, such as the user's inner thighs).

The static coefficient of friction may be varied by adding coatings or layers having a high coefficient of friction, by mechanically deforming the substrate to create a rougher surface, or by any other means known in the art.

Test Methods

All testing is performed at 23°±2° C. and 50±2% relative humidity, unless otherwise specified. All samples are equilibrated at that environment for at least 2 hours before testing.

Water Vapor Transmission Rate

Water Vapor Transmission rate (WVTR) is measured according to EDANA/INDA Worldwide Strategic Partners Method WSP 70.4 (08) using a Permatran-W model 100K (MOCON, Minnesota, Minn.). The test method was run as per the WSP standard test, using a test apparatus temperature of 37.8° C., a nitrogen flowrate of 120 SCCM, and the standard mode with 2 cycles and 5 minute exam time. Each cell is individually adjusted to a relative humidity (RH) of 60%±1.5%. The standard reference film (S/N 1008WK089 from MOCON) should be run prior to testing the samples in order to ensure that the equipment is running properly. The standard reference film results should be within ±10% of the values reported by MOCON.

Using scissors or a die cut a specimen 35 mm in diameter. If the outer cover is multilayered the specimen is run as the composite sample. The side of the outer cover which normally faces the skin is oriented toward the water for testing. Report the WVTR as $g/m^2/24$ hr to the nearest 1 $g/m^2/24$ hr.

Hydrostatic Head Test

Hydrostatic head test is conducted as described in EDANA/INDA Worldwide Strategic Partners Method WSP 80.6 (50) using a TexTest FX 3000 Hydrostatic Head Tester. The test was performed using the 100 $cm^2$ test head, with a water temperature of 23±2 C.°. The test was modified to increase the pressure at a rate 20 mbar/min. The test was terminated and pressure recorded after 3 separate drops are formed on the surface of the specimen. These drops must form in three different penetrating holes, and must originate 6 mm away from the edge of the clamp.

Using scissors, a specimen 14 cm by 14 cm is cut from the outer cover. If the outer cover consist of multiple layers, the layers are tested as a composite. The side of the outer cover which normally faces the skin is oriented toward the water for testing. If the size of the outer cover will not permit sampling of a 14 cm by 14 cm specimen, use instead a 10 cm by 10 cm sample and a 28 $cm^2$ test head. Report the Hydrostatic head pressure to ±0.1 mbar.

Whole Product Back Extension Forces

Whole product back extension forces are measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with 1 inch×1 inch diamond faced grips.

As used herein 100% strain means that the sample has been elongated by 100% of its original length measured under no applied load. For example, a sample with an original length of 100 mm will have a 100% strain when elongated to a length of 200 mm.

Program the tensile tester to extend the specimen to 100% strain at a rate of 254 mm/min., hold at that strain for 30 sec. and then return to 0% strain at 254 mm/min. After 60 sec. again extend the sample to 100% strain at 254 mm/min., hold for 30 sec. and then return to 0% strain at 254 mm/min. Set the data acquisition rate to 100 Hz. From the force versus % strain curve, program the software to report the extension (mm) at 5N of force on the first load cycle, the % strain (%) at 5N of force on the first load cycle, and the force (N) at 25% strain on the first unload cycle.

For a taped-type absorbent article: Set the gage length to the length 195 as shown in FIG. 1. Zero the crosshead. Insert the specimen into the upper grips, aligning edge 154 of the panel that is proximal to longitudinal centerline 12 with the lower edge of the grip face and close the grips. Zero the load cell. Insert the other end of the specimen into the lower grips aligning edge 154 of the panel that is proximal to longitudinal centerline 12 with the upper edge of the grip face, and close the grips. The specimen should be under enough tension to eliminate any slack in the sample, but force measured by the instrument must be less than 0.5N. Start the tensile tester's program, and record data.

For a pants-type absorbent article: Measure the waist circumference of the article. Divide the waist circumference by 2 to calculate a back waist length. Fold the article such that the front or top portion of the waist and the back or bottom portion of the waist are of equal length (i.e., the waist circumference divided by 2). Set the gage length to the back waist length. Zero the crosshead. Insert the specimen into the upper grips, aligning the edge of the waist of the folded article with the lower edge of the grip face and close the grips. Zero the load cell. Insert the other end of the specimen into the lower grips aligning the edge of the waist of the folded article with the upper edge of the grip face, and close the grips. Make a T-shaped cut longitudinally through the front waist and laterally through the crotch of the article, such that the front and rear waist portions are separated. The specimen should be under enough tension to eliminate any slack in the sample, but force measured by the instrument must be less than 0.5N. Start the tensile tester's program, and record data.

For a front waist measurement: Measure the waist circumference of the article. Divide the waist circumference by 2 to calculate a front waist length. Fold the article such that the front or bottom portion of the waist and the back or top portion of the waist are of equal length (i.e., the waist circumference divided by 2, or the lesser of the front and back waist lengths). Set the gage length to the front waist length. Zero the crosshead. Insert the specimen into the upper grips, aligning the edge of the front waist of the folded article with the lower edge of the grip face and close the grips. Zero the load cell. Insert the other end of the specimen into the lower grips aligning the edge of the front waist of the folded article with the upper edge of the grip face, and close the grips. For a pants-type article, make a T-shaped cut longitudinally through the back waist and laterally through the crotch of the article. The specimen should be under enough tension to eliminate any slack in the sample, but force measured by the instrument must be less than 0.5N. Start the tensile tester's program, and record data.

Report extension (mm) at 5N of force on the first load cycle to ±1 mm, the % strain (%) at 5N of force on the first load cycle to ±0.1%, and the force (N) at 25% strain on the first unload cycle to ±0.1 N.

Outer Cover Composite Extension Force

The Outer Cover Composite Extension Forces are measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with rubber faced grips wider than the width of the specimen. The gage length is 25.4 mm and the data acquisition rate is 100 Hz.

Program the tensile tester to extend the specimen to 110% strain at a crosshead speed of 254 mm/min. and then return to the original crosshead position. Program the software to report the force (N) at 50% strain and 100% strain.

Using a JDC precision cutter (Thwing Albert) cut a 1" wide strip in the longitudinal direction of the outer cover that is 3" long. If there are multiple layers of the outer cover the specimen should be cut though all layers. The composite should be tested as a whole and also as the individual layers. Any single specimen (either composite or single layer) should only be tested once.

Set the gage length to 25.4 mm, zero the crosshead and zero the load cell. Insert the specimen into the upper grips, aligning it vertically within the upper and lower jaws and close the upper grips. Insert the specimen into the lower grips and close. The specimen should be under enough tension to eliminate any slack, but less than 0.05N of force on the load cell. Start the tensile tester's program and collect data.

Report the force (N) at 50% extension for the composite (multi-layered) specimen to ±0.01 N. Report the force (N) at 100% extension for each of the single layered specimens to ±0.01 N.

Coefficient of Friction

The static coefficient of friction can be measured using ASTM Method D 1894-01 with the following particulars. The test is performed on a constant rate of extension tensile tester with computer interface (a suitable instrument is the MTS Alliance using Testworks 4 Software, as available from MTS Systems Corp., Eden Prairie, Minn.) fitted with a coefficient of friction fixture and sled as described in D 1894-01 (a suitable fixture is the Coefficient of Friction Fixture and Sled available from Instron Corp., Canton, Mass.). The apparatus is configured as depicted in FIG. 1.c of ASTM 1894-01 using a stainless steel plane with a grind surface of 320 granulation as the target surface. A load cell is selected such that the measured forces are within 10% to 90% of the range of the cell. The tensile tester is programmed for a crosshead speed of 127 mm/min, and a total travel of 130 mm. Data are collected at a rate of 100 Hz.

The test specimen is cut into a square 6.35 cm by 6.35 cm with its sides parallel and perpendicular to the longitudinal axis of the outer cover. The specimen is mounted onto the foam rubber side of the sled using double sided adhesive tape (tape should be wide enough to cover 100% of the sled's surface). The specimen is oriented on the sled such that the skin facing surface of the outer cover will face toward the target surface and the longitudinal axis of the outer cover is parallel to the pull direction of the sled. The mass of the sled with mounted sample is recorded to 0.1 gram. The surface of the stainless steel plane is cleaned with isopropanol between each analysis. To measure the static coefficient of friction against skin, the target surface is Naturin Coffi Film, Product #101183, available from Globe Casing Company of Carlstadt, N.J. To measure the static coefficient of friction against the absorbent insert, the target surface is an 18 gsm matte polypropylene film from Clopay Plastics Products Company of Mason, Ohio.

The Static COF is calculated as follows:

$$\text{Static COF} = A_S/B$$

$A_S$=maximum peak force in grams force (gf) for the initial peak
B=mass of sled in grams AATCC Test Method 124-2001, Modified In a wash cycle, a component of an absorbent article, such as an outer cover, is machine washed and machine dried according to the protocol from AATCC (American Association of Textile Chemists and Colorists) Test Method 124-2001, with the selected parameters and variations listed below.

a) Per section 6, Apparatus and materials, a Kenmore 600 (Heavy Duty—Super Capacity Plus—Quiet Pak) is used for the automatic washing machine, and a Maytag Commercial (such as model numbers MDE27MNACW, MDE15MNAYW, and MDE13MNACW) is used for the automatic tumble dryer.

b) Despite the instructions in Section 6, Apparatus and materials, the following ballast is used: Test Fabric style 493 from Testfabrics, Inc, West Pittston, Pa., which is cotton sheeting, with a thread count of 60×60, a weight of 151 gsm, and a size of 55' by 39".

c) Despite the instructions in Section 6, Apparatus and materials, the evaluation area is not configured according to section 6.7 and the apparatus of section 6.8 is not used. Instead, all visual evaluations are performed under typical artificial lighting conditions (e.g. fluorescent light), which allows a person with normal vision to clearly see.

d) Despite the instructions in Section 7, Test Specimen, the component to be tested is (as necessary) entirely removed from the rest of the absorbent article, and (to the extent allowed by the removal) the component is tested as an undamaged whole. Up to three components of the same type are washed simultaneously.

e) Regarding the machine wash in Section 8.2.2, use the "large" setting on the machine for the water level, select a wash temperature of 32+/−3° C. (90+/−5° F.), and a rinse temperature of 16+/−3° C. (60+/−5° F.).

f) Regarding the settings in Section 8.2.2, select Normal/Cotton Sturdy, which has a washing time of 12 minutes, an initial spin time of 6 minutes, a refill time of 4 minutes, a rinse time of 5 minutes, and a final spin cycle time of 6 minutes.

g) Regarding the Drying in Section 8.3, select Cotton Sturdy and Whites & Colors.

h) Despite the instructions in Section 8.5, the steps of conditioning and preconditioning are not performed.

i) Despite the instructions in Section 9, Evaluation, these evaluation steps are not performed. Instead, the tested component is evaluated by one of skill in the art, to determine whether the testing has resulted in significant degradation to the appearance or performance of the article that would render it unsuitable for its intended functionality and/or use.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A reusable outer cover for an absorbent article, the reusable outer cover comprising:
   a front zone;
   a crotch zone, wherein the crotch zone has a wearer-facing surface comprising a first layer and a garment-facing surface comprising a second layer, and the second layer is more hydrophobic than the first layer; and
   a rear zone;
   wherein the crotch zone has a higher WVTR than the front and rear zones.

2. The reusable outer cover of claim 1, wherein the crotch zone has a WVTR of at least 1200 g/m²/24 hrs.

3. The reusable outer cover of claim 2, wherein the crotch zone has a WVTR of at least 3000 g/m²/24 hrs.

4. The reusable outer cover of claim 1, wherein the crotch zone has a higher fluid penetration resistance than the front and rear zones.

5. The reusable outer cover of claim 4, wherein the crotch zone has a fluid penetration resistance of at least 5 mbar.

6. The reusable outer cover of claim 1, wherein the second layer is more hydrophobic than the front and rear zones.

* * * * *